(12) United States Patent
Stumpe et al.

(10) Patent No.: US 7,612,879 B2
(45) Date of Patent: Nov. 3, 2009

(54) METHOD AND DEVICE FOR THREE-DIMENSIONALLY DETERMINING THE REFRACTIVE INDEX OF TRANSPARENT OR PARTIALLY TRANSPARENT LAYERS

(75) Inventors: Joachim Stumpe, Nauen (DE); Christoph Jung, Bayreuth (DE); Olga Kulikovska, Berlin (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 360 days.

(21) Appl. No.: 10/559,650

(22) PCT Filed: Jun. 1, 2004

(86) PCT No.: PCT/EP2004/005911

§ 371 (c)(1),
(2), (4) Date: Oct. 30, 2006

(87) PCT Pub. No.: WO2004/109260

PCT Pub. Date: Dec. 16, 2004

(65) Prior Publication Data

US 2007/0097356 A1    May 3, 2007

(30) Foreign Application Priority Data

Jun. 5, 2003 (EP) .................. 03012198

(51) Int. Cl.
*G01J 4/00* (2006.01)
(52) U.S. Cl. .................. 356/364
(58) Field of Classification Search ......... 356/364–369, 356/128, 432
See application file for complete search history.

(56) References Cited

U.S. PATENT DOCUMENTS 3,963,348 A   6/1976   Ito et al.

(Continued)

FOREIGN PATENT DOCUMENTS

JP   03 195905   8/1991

(Continued)

OTHER PUBLICATIONS

Bortchagovsky E.G., "Ellipsometric Method for Investigation of the Optical Anisotropy of Thin Films: Theory and Calculations", Thin Solid Films, Elsevier-Sequoia S.A. Lausanne, CH, vol. 307, No. 1-2, Oct. 10, 1997, pp. 192-199.

(Continued)

*Primary Examiner*—L. G Lauchman
(74) *Attorney, Agent, or Firm*—Venable LLP; Robert Kinberg; Justine A. Gozzi (57) ABSTRACT

The present invention relates to a method and a device for three-dimensionally determining the refractive index and, if necessary, the layer thickness of transparent or partially transparent layers in which the layer (1) is irradiated at different angles of incidence (5) with polarised light, and variations in the polarisation of the light are measured and evaluated as the light passes through the layer (1). The method is characterized in that the measurement is carried out through an immersion medium (3) between which the layer (1) is inserted. A highly accurate determination of the refractive index of anisotropic thin layers in all three spatial directions is made possible by this method.

13 Claims, 3 Drawing Sheets

U.S. PATENT DOCUMENTS 5,526,118 A    6/1996    Miyagawa et al.

FOREIGN PATENT DOCUMENTS

JP    11 037937    2/1999
WO    WO 01/42769    6/2001

OTHER PUBLICATIONS

Bortchagovsky E.G. et al., "Comparison of Ellipsometric Methods for Separate Determiination of Thickness and Optical Constants of Thin Films", Folia Biolgoica, vol. 4517, Jun. 5, 2000, pp. 126-133.
Jung C.C. et al., "Three Dimensional Anisotropies Induced by Light In Thin Polymer Films", Proc. Spei—Int. Soc. Opt. Eng. (USA), Proceedings of The Spie—The International Society for Optical Engineering, 2003, Spie—Int. Soc. Opt. Eng. USA, vol. 5212, No. 1, Aug. 4, 2003, pp. 83-93.
Ramsdale et al., "Ellipsometric Determination of Anisotropic Optical Constants In Electroluminescent Conjugated Polymers", Advanced Materials, VCH, Verlagsgesellschaft, Weinheim, DE, vol. 14, No. 3, Feb. 5, 2002, pp. 212-215.
T. Srikhirinm, "An Investigation of the Photoinduced Changes of Absorption of High-Performance Photoaddressable Polymers", Chemphyschem, vol. 3, 2002, pp. 335-345.
Patent Abstracts of Japan, vol. 1999, No. 5, May 31, 1999.
Patent Abstracts of Japan, vol. 15, No. 460, Nov. 21, 1991.
C.C. Jung, "Light-Induced Generating and Characterization of the Optical Anisotropism," Doctoral Dissertation, Fraunhofer-Institut fur Angewandte Polymerforschung Arbeitsgruppe Priv.-Doz. Dr. J. Stumpe, Postdam, Apr. 18, 2004.

METHOD AND DEVICE FOR THREE-DIMENSIONALLY DETERMINING THE REFRACTIVE INDEX OF TRANSPARENT OR PARTIALLY TRANSPARENT LAYERS

TECHNICAL SCOPE

The present invention relates to a method and device for three-dimensionally determining the refractive index of transparent or partially transparent layers, wherein the layer is irradiated with polarised light at different angles of incidence, and variations in the polarisation of the light are measured and evaluated as it passes through the layer.

Methods of this kind are known by the term transmission ellipsometry or transmission polarimetry. In this method the layer is irradiated with polarised light, and a rotation of the light polarisation is recorded. The measuring device used generally contains a light source, at least one polariser in front of and behind the mass volume for the sample, as well as a photo detector which measures the light intensity occurring in different positions of the polarisers.

In the field of optical technologies in which anisotropic layers with defined optical properties are required, the determination of the three-dimensional refractive index of optically anisotropic layers is playing an increasingly important role. The anisotropic optical properties of thin layers or films, for example, are therefore extremely important in display technology. Very thin layers are of great interest in nanotechnology. Thicker films are also used as wave guides for optical information processing. More recent fields of application relate to the fields of optical safety elements and reversible optical data storage. A concrete example of applications of the generic method is the determination of the three-dimensional anisotropy of thin layers which are used directly as optical components, e.g. as retarders or polarisers in flat screens, or which are used as photo alignment layers for manufacturing these components in order to be able to measure or control the dependence of the display on the angle of vision.

Methods have recently been developed for adjusting the anisotropy of thin polymer layers by means of polarised light in a defined manner and for amplifying this anisotropy by tempering in the liquid crystalline phase (cf. for example J. Stumpe et al., SPIE Vol. 3800, 1999, pages 150-163). Three-dimensional determination of the refractive index in the layer is necessary to verify the result of this manufacturing process. Here an extremely accurate determination of the refractive index in all three spatial directions, even after irradiation, is very important for being able to estimate the result of the subsequent self-organisation process brought about by tempering.

STATE OF THE ART

Various methods are now known for determining the refractive index of layers. For example, the three-dimensional anisotropy of the layer for absorbing samples can be determined by means of UV spectroscopy at a variable angle of incidence, as described, for example, in T. Srikhirin et al., ChemPhysChem, 2002, 3, pages 335-342. Here the thin layer is applied to a glass substrate and measured with the glass substrate between two hemispheres of a material with a suitable refractive index. Because of this immersion technique angle-dependent reflection losses on the interfaces are reduced, the avoidance of which is very important, particularly in absorption spectroscopy. The UV spectroscopy for determining the three-dimensional anisotropy is only suitable, however, if adequate absorbing layers are provided.

Ellipsometric methods, with which anisotropy is recorded on the basis of double refraction in the layer, are therefore used for transparent layers, particularly for layer thicknesses of 1 µm or less. For example C. C. Jung et al., Mol. Cryst. Liqu. Cryst., 2002, Vol. 375, pages 713-721, employ the so-called prism coupler method with polarised light to measure layers with a layer thickness of approximately 1 µm. Here wave guide modes in the layer are excited by coupling the light via a prism at angles of incidence which are determined by the refractive indices of the layer. If a prism with a high refractive index is used here, the refractive index in the layer perpendicular is also accessible with light polarised in parallel with the plane of incidence due to the refraction in the layer. Unfortunately wave guide modes only exist in the case of optical layer thicknesses (n×d) which exceed the wavelength of the light used. In order to be able to determine the absolute refractive index and the layer thickness separately, thicknesses at least twice as thick are required.

A further method for three-dimensional determination of the refractive index of layers is known from C. M. Ramsdae et al., Adv. Mat., 2002, 14 (3), pages 212-215. In this method a combination of reflection ellipsometry and transmission ellipsometry is used at a variable angle of incidence in order to improve the accuracy of the measurement method. However, this method is not yet producing sufficiently accurate results in practice when measuring thin transparent layers in many applications.

This also suffers from ambiguities which arise in the measurement of thin anisotropic layers by means of ellipsometry, as also stated in E. G. Bortchagovsky, Thin Solid Films 307 (1997), 192-199. In this publication, which deals with theoretical calculations for reflection ellipsometry, it is suggested that in order to avoid this problem, the reflective properties of the substrate used should be specifically influenced by covering with a thick transparent layer.

The object of this invention is to indicate a method and device for three-dimensionally determining the refractive index of thin transparent or partially transparent layers which enable the refractive index in all three spatial directions to be measured with a high degree of accuracy.

REPRESENTATION OF THE INVENTION

The object is achieved with the method according to embodiments of the invention. Advantageous designs of the method and device constitute the object of the dependent claims, or may be derived from the following description and the embodiments.

In this method for three-dimensionally determining the refractive index and, if necessary, the layer thickness (when combined with reflection ellipsometry) of transparent or partially transparent layers, the layer is irradiated with polarised light by a known method, at different angles of incidence, and variations in polarisation of the light are measured and evaluated as it passes through the layer. This method is characterised in that the measurement is carried out through an immersion medium in which the layer is inserted, if necessary applied to a transparent carrier substrate. Here the layer to be measured is also understood to be a system of layers consisting of several layers, a foil or a film. Immersion medium is understood in this patent application to refer to a medium which results in a jump in the refractive index which is reduced compared with the air/layer or air/substrate transition, i.e. has a refractive index that is higher (preferably by at least 0.1) than air. A liquid or solid immersion medium is preferably chosen with a refractive index which is at least approximately equal (preferably with a difference of less than 0.1) to the refractive index of the substrate and/or the expected mean refractive index of the layer to be measured.

Surprisingly the accuracy in determining the refractive index in the three spatial directions can be increased by two orders of magnitude relative to the conventional transmission ellipsometry by applying this method when measuring thin transparent layers. This enables optical anisotropy to be determined in the three spatial directions and the refractive index ellipsoid to be tilted highly accurately. The method also enables the absolute refractive index of the measured layer to be determined. Compared with the reflection ellipsometry method, the additional advantage lies in the insensitivity to ultra-thin surface layers which are formed on the layer to be characterised and are capable of distorting the measurement because of other optical properties.

The method is particularly suitable for measuring thin transparent or partially transparent layers with a layer thickness of less than 1 μm. Accurate optical determination of three-dimensional anisotropy at wavelengths for which the film is transparent is only possible for very thin layers of less than 50 nm. In the case of thicker films or layers, gradients, including tilt gradients, can be determined more accurately than with the methods used hitherto.

The ellipsometric measurements are evaluated in a similar manner to transmission ellipsometry methods of prior art at a variable angle of incidence. If the method is combined with reflection ellipsometry, an improvement in layer thickness determination is achieved. For this purpose the parameters to be determined are adapted iteratively with a biaxial model to both measurements so that the layer thickness is always taken from the reflection measurement (in the case of a fixed mean refractive index, from the transmission measurement), and the refractive index is always taken from the transmission measurement (in the case of a fixed layer thickness from the reflection measurement). Normal methods of layer thickness measurement, e.g. raster force microscopy may also be used to determine the layer thickness of the measured layer required for the evaluation.

The method may also be used for determining the complex refractive index of the layer by working with several different wavelengths. This can be achieved by the irradiation of monochromatic light which is adapted in the wavelength. Furthermore, light of a larger bandwidth can be irradiated from which the wavelength in question is filtered for the measurement and varied in time with an adaptable wavelength-selective element, e.g. a monochromator, before the light hits the layer. When a light source with a larger bandwidth is used, the measurement can also be carried out simultaneously for several wavelengths by inserting a dispersive element spatially splitting the wavelengths, e.g. a prism, in the path of rays before the layer, and by measuring the proportions spatially split in this manner simultaneously and independently by means of a suitably arranged detector array after the layer has passed through.

In an advantageous design of this method a liquid is used as the immersion medium. This liquid is poured into a chamber in which the layer is measured on the transparent substrate. The angle of incidence of the polarised light beam conducted through the chamber onto the layer can be varied for the measurement by rotating the substrate with the applied layer, referred to in the following as the sample, in the chamber, e.g. by a manual mechanical engagement technique or by means of a torque motor. The polarised light beam is also referred to in the following as the measuring beam.

In a further design of this method two transparent solid body halves are used as the immersion medium. Both these solid body halves are brought into contact with the layer and the substrate with their flat surfaces facing the substrate or layer by means of an immersion fluid, and are rotated together with the sample in the measuring beam. Here the rotation may be effected in the same manner as in the preceding design. Two hemispheres, e.g. of glass, or two semi-cylinders may be used as solid body halves. If semi-cylinders are used, the direction of rotation is limited to one dimension in order to guarantee a vertical incidence of the measuring beam onto the surface of this immersion medium in any angular position. Here the two solid body halves are supported so that they are as free of tension as possible, to avoid strain double refraction. In a particularly advantageous design the solid body halves are not loaded with a compressive force in the direction of the sample during measurement. Instead the action of the capillary forces of the immersion fluid is used to provide adequate combined support of the sample and solid body halves.

The present device for carrying out the method has a transmission measuring device for measuring a variation in polarisation as polarised light, the measuring beam, passes through a sample, and a rotating device for the sample. Such a transmission measuring device consists, for example, of a light source, one or more polarisers in front of and behind the measuring volume for the sample, and a photo detector for measuring the intensity transmitted. The device also has a support for an immersion medium which is designed so that the sample can be inserted in the immersion medium and can be rotated in or with the immersion medium relative to the beam axis of the measuring beam.

In an advantageous design of this device the support is formed by a chamber for a liquid immersion device which has inlet and outlet surfaces for the measuring beam. In this design the sample can be rotated in the immersion medium, and hence in the measuring beam, by a rotary pin on which the sample is supported. An alternative design provides a cylindrical chamber into which the sample is inserted. In this design the entire chamber can be rotated together with the sample in the measuring beam, e.g. by means of a rotary plate on which the chamber rests. In a further advantageous design the support is designed for receiving and fixing the two solid body halves which form the immersion medium and are connected to the rotating device.

The support with the rotating device can obviously also be provided separately and inserted in existing transmission ellipsometers.

BRIEF DESCRIPTION OF THE DRAWINGS

The present method and the associated device are explained briefly once again with reference to embodiments in conjunction with the drawings, in which.

METHODS OF CARRYING OUT THE INVENTION

Figure 1:
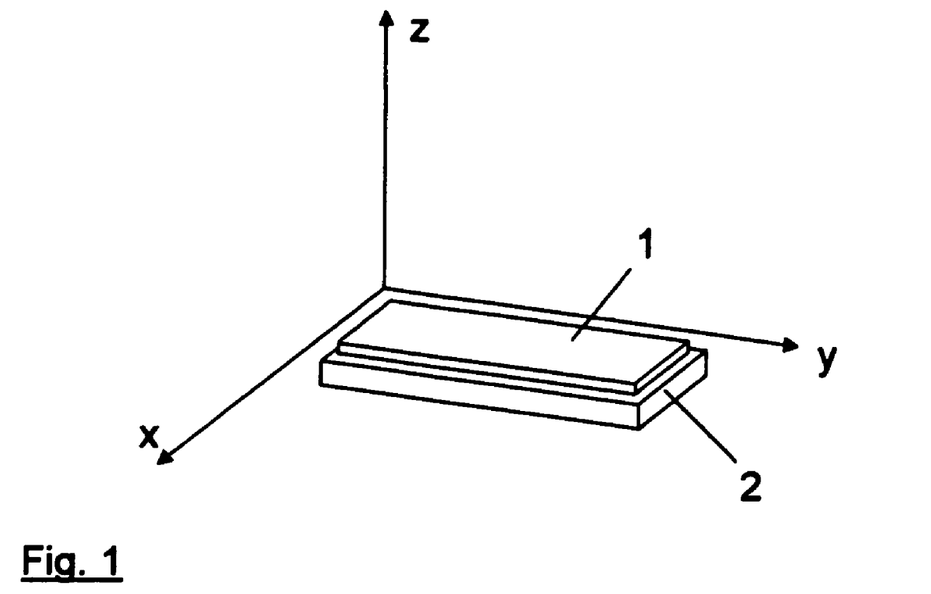
FIG. 1 shows a representation of a layer to be measured on a carrier substrate with the assigned system of axes.
Figure 2:
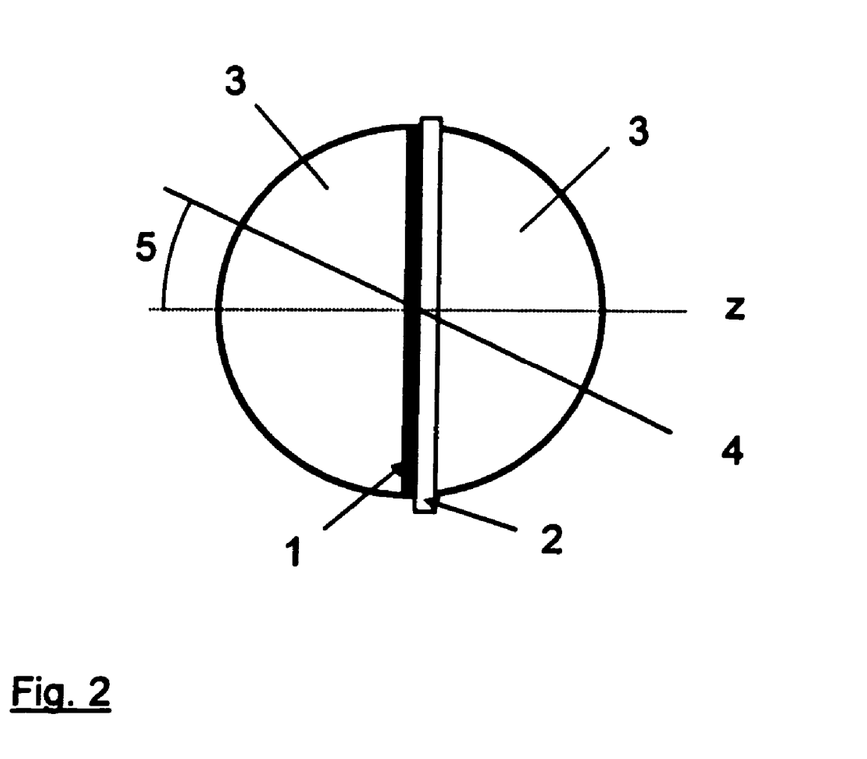
FIG. 2 shows an example of a section from a measuring device or device for carrying out the present method.

FIG. 1 shows, as an example, a sample consisting of the anisotropic layer 1 to be measured, which has been centrifuged onto a carrier substrate 2, in this example a quartz glass carrier. A 137.7 mm thick polymer layer, an azobenzene side chain polymer, is used as the exemplary layer 1. The refractive indices of layer 1 are determined in all three spatial directions (x, y, z) by the present method. For this purpose the sample is inserted in or between an immersion medium with at least a similar refractive index to carrier substrate 2. This can be achieved by means of solid body halves, e.g. hemispheres, semi-cylinders or prisms, combined with an immersion liquid. One example of this is shown in FIG. 2. In an alternative design, the sample can also be inserted in a chamber, which is filled with an immersion liquid or is filled as illustrated in FIG. 3.

FIG. 2 shows a first example of a section from a measuring device according to this invention. Here use is made of two hemispheres 3 from the material of carrier substrate 2, in this example glass, between which the sample is inserted. Hemisphere 3 arranged on the side of substrate 2 has a central height reduced by the substrate thickness so that the two hemispheres 3 form a sphere with the sample arranged between them. The thickness of layer 1 to be measured, 137.7 nm, is negligible. Before the two hemispheres 3 are connected to the sample, an immersion oil is poured between the two hemispheres 3 and the sample. The entire arrangement with the sample is fixed by a support not shown in the figure, which is connected to a rotating device for rotating the sample in measuring beam 4. The support is designed so that strain double refraction in hemispheres 3 is avoided. For this purpose the support may either in contact only with the sample, where hemispheres 3 and the sample are only held together by the capillary forces of the immersion liquid, or are in contact with hemispheres 3, where only light pressure is exerted on hemispheres 3 by means of weak springs or with finely adjustable screws. By rotating the sample with hemispheres 3 in measuring beam 4, angle of incidence 5 of measuring beam 4 onto layer 1 can be varied during the measurement in order to carry out the measurement with different angles of incidence.

Figure 3:
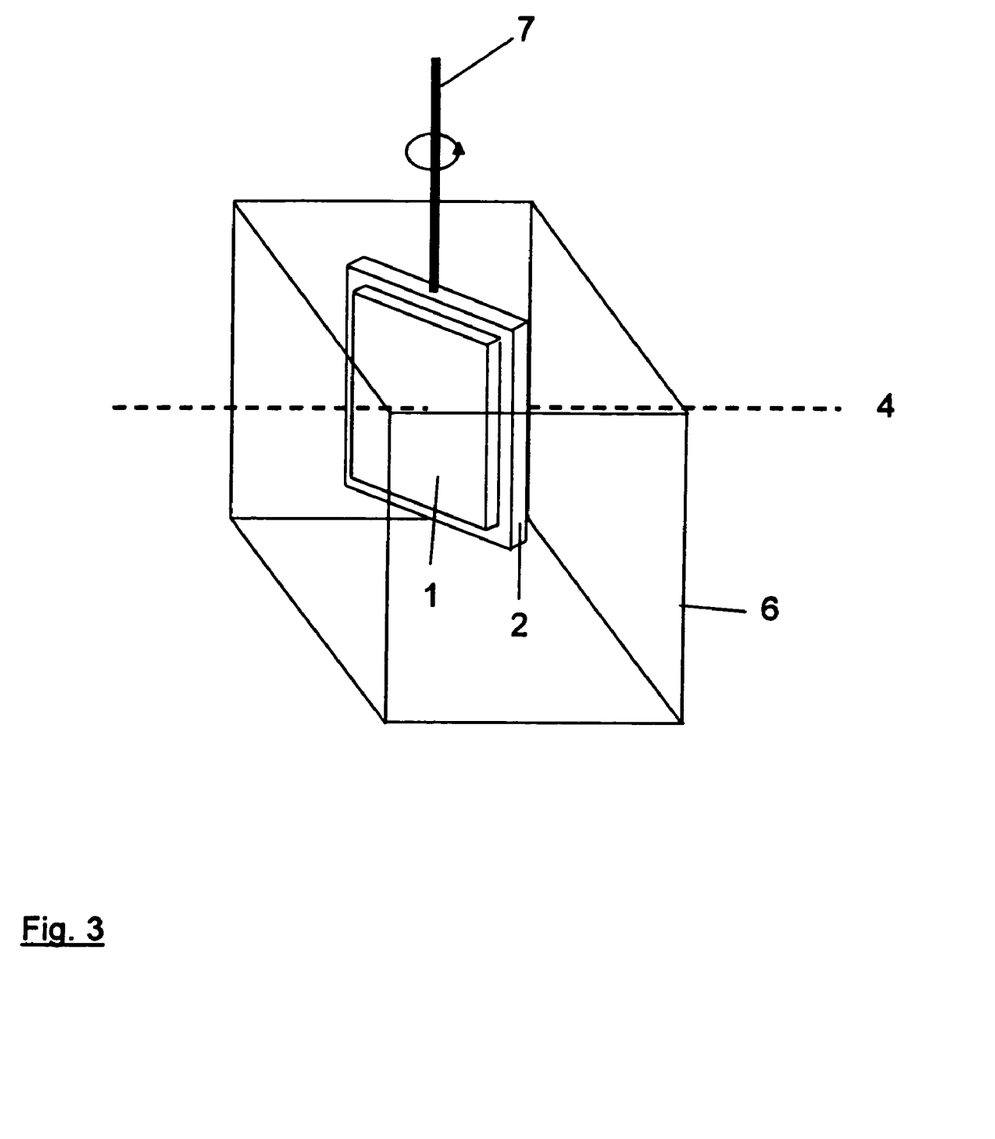
FIG. 3 shows a further example of a section from a measuring device or device for carrying out the present method.

A further example of a section from a device according to this invention is shown in FIG. 3. This part of the device consists of a chamber 6 in which a rotary support for the samples fitted by means of a rotary pin 7. Chamber 6 is then filled with an immersion liquid and is designed so that measuring beam 4 is able to be fed through chamber 6 and the sample. For this purpose chamber 6 can be designed with an inlet window perpendicular to measuring beam 4 and an outlet window parallel with the inlet window, where both windows can be provided with anti-reflection layers. Rotary pin 7 may either be inserted in the chamber by a through opening with a seal or immersed in the liquid from above without a seal, as achieved in this example. This measuring device has the advantage of a simple structure and avoids the problem of strain double refraction in the immersion medium. To avoid any variation in the refractive index of the immersion liquid by evaporation, chamber 6 can also be provided with a sliding cover which in the centre has a through opening for rotary pin 7.

Figure 4:
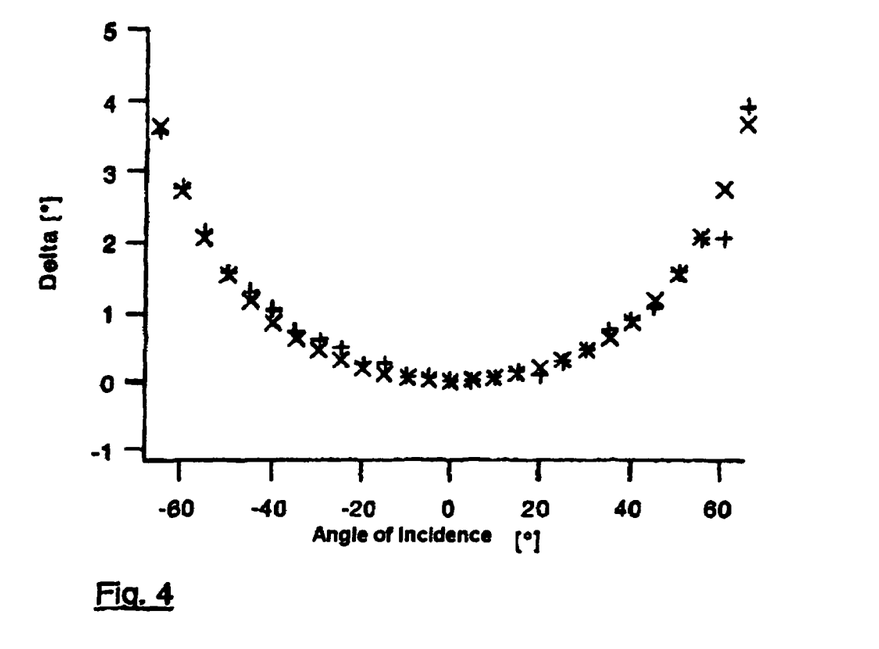
FIG. 4 shows an example of the result of the measurement of a polymer layer 137.7 mm thick compared with theoretical values.

FIG. 4 shows the result of a transmission ellipsometry measurement by the method of this invention on the sample already presented. The measurement was carried out with a measuring device according to FIG. 2, where hemispheres 3 were held together by the capillary force of the immersion oil. The measuring curve clearly shows the increase in the ellipsometric measurement parameter Δ, which describes the difference in path between s- and p-polarised light as the angle of incidence increases. This increase corresponds to a preferred orientation in the plane of the measured layer, adhering to the correct prefix. The result obtained from this measurement indicates $n=n_x+n_y+n_z=1.5681$ (1) as the average refractive index and $\Delta n_{zx}=n_z-n_x=-0.0259$ as double refraction in the z-direction. The superposition with the points obtained by theoretical modelling for these values can be seen in the figure.

Figure 5:
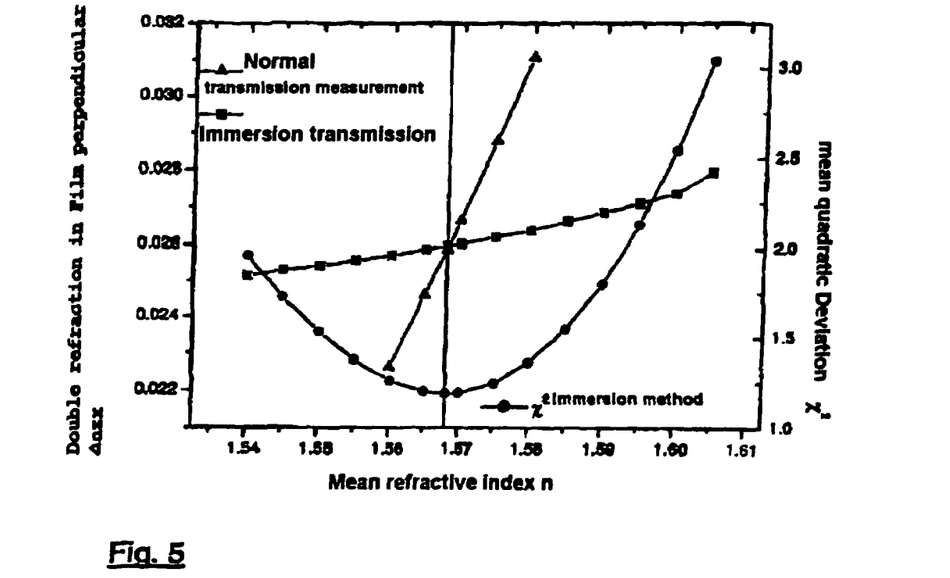
FIG. 5 shows a comparison of the measured results after evaluation of the measurement according to FIG. 4 measured results, as obtained with a normal transmission ellipsometric measurement of the same sample.

Finally, FIG. 5 shows a comparison of the results of this measurement with the result of a measurement on the same sample, which was carried out by normal transmission ellipsometry without an immersion liquid. For the evaluation the average refractive index n is assumed to be fixed for both measurements, and the double refraction in the z-direction is determined by adaptation to the theoretical curve. This ensures the dependence on n and $\Delta n_{zx}$, as shown in FIG. 5. The measuring curves, with and without immersion, intersect exactly for the refractive index n, which was already predicted by this method. This shows that both the absolute refractive index and the anisotropy of a thin layer can be determined by the present method. For a comparison the deviation between theoretical and experimental values is also plotted as mean quadratic deviation in FIG. 5. The excellent correspondence of the minimum mean quadratic deviation with the point of intersection of the measurements from this method and the transmission measurement without immersion can be seen. Such a minimum is not attained when the conventional transmission ellipsometry is carried out (not shown in the figure), so that an absolute refractive index of 1.584 and a $\Delta n_{zx}$ of −0.0327 would result from an evaluation of the normal measurement without immersion by means of a free adaptation. These values differ considerably from the actual values.

| LIST OF REFERENCES | |
|---|---|
| 1 | Layer to be measured |
| 2 | Carrier substrate |
| 3 | Hemispheres as immersion medium |
| 4 | Measuring beam |
| 5 | Angle of incidence |
| 6 | Chamber |
| 7 | Rotary pin |

The invention claimed is:

1. A method for three-dimensionally determining a refractive index of a transparent or partially transparent layer via transmission ellipsometrie, comprising:
   inserting the layer in an immersion medium which has a higher refractive index than air;
   irradiating the layer with polarised light at different angles of incidence; and
   measuring and evaluating variations in the polarisation of the light as the light passes through the layer.

2. A method according to claim 1, further comprising applying the layer to a transparent substrate, wherein the measuring is on the substrate.

3. A method according to claim 2, further comprising using a refractive index of the immersion medium which at least corresponds approximately to a refractive index of the substrate.

4. A method according to claim 1, further comprising inserting a liquid immersion medium into a chamber, wherein the measuring is in the chamber.

5. A method according to claim 1, further comprising forming the immersion medium with two solid body halves between which the layer is inserted.

6. A method according to claim 5, further comprising supporting the two hemispheres or hemi-cylinders as the immersion medium.

7. A method according to claim 6, further comprising supporting the two hemispheres or hemi-cylinders with capillary forces on the layer and the substrate.

8. A method according to claim 1, further comprising determining a complex refractive index by irradiating the layer simultaneously or consecutively with light of different wavelengths.

9. A method for measuring layers for flat screens, optical data storage or optical wave guides comprising: utilizing the method according to claim 1.

10. A device for carrying out the method according to claim 1, comprising:
   a transmission measuring device for measuring a variation in polarisation as polarised light passes through a sample; and
   a rotating device for rotating the sample, wherein the rotating device comprises:
      an immersion medium which has a higher refractive index than air, and
      a support for the immersion medium so that the sample is insertable within the immersion medium and the sample is rotatable in or with the immersion medium relative to a beam axis of the polarised light.

11. A device according to claim 10, wherein the support comprises a chamber for a liquid immersion medium, the chamber having inlet and outlet surfaces for the polarised light.

12. A device according to claim 11, wherein the chamber comprises a cylindrical shape and is connected to the rotating device so that the chamber is rotatable by the rotating device.

13. A device according to claim 10, wherein the support is connected to the rotating device, wherein the support receives and fixes two solid body halves, the two solid body halves forming the immersion medium

* * * * *

UNITED STATES PATENT AND TRADEMARK OFFICE
CERTIFICATE OF CORRECTION

| | |
|---|---|
| PATENT NO. | : 7,612,879 B2 |
| APPLICATION NO. | : 10/559650 |
| DATED | : November 3, 2009 |
| INVENTOR(S) | : Stumpe et al. |

It is certified that error appears in the above-identified patent and that said Letters Patent is hereby corrected as shown below:

Col. 7, lines 4-5; In the Claims:

In Claim 6, lines 1-2, replace ~~supporting the two hemispheres~~ with <u>using two hemispheres</u>.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO.      : 7,612,879 B2
APPLICATION NO. : 10/559650
DATED           : November 3, 2009
INVENTOR(S)     : Stumpe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 645 days.

Signed and Sealed this

Nineteenth Day of October, 2010

David J. Kappos
*Director of the United States Patent and Trademark Office*